United States Patent
Hanada

(10) Patent No.: US 10,168,403 B2
(45) Date of Patent: Jan. 1, 2019

(54) MAGNETIC RESONANCE IMAGING APPARATUS

(71) Applicant: HITACHI, LTD., Tokyo (JP)

(72) Inventor: Hikaru Hanada, Tokyo (JP)

(73) Assignee: HITACHI, LTD., Tokyo (JP)

( * ) Notice: Subject to any disclaimer, the term of this patent is extended or adjusted under 35 U.S.C. 154(b) by 322 days.

(21) Appl. No.: 15/032,698

(22) PCT Filed: Oct. 30, 2014

(86) PCT No.: PCT/JP2014/078885
§ 371 (c)(1),
(2) Date: Apr. 28, 2016

(87) PCT Pub. No.: WO2015/076082
PCT Pub. Date: May 28, 2015

(65) Prior Publication Data
US 2016/0266221 A1  Sep. 15, 2016

(30) Foreign Application Priority Data
Nov. 22, 2013  (JP) .................................. 2013-242181

(51) Int. Cl.
*G01R 33/36* (2006.01)
*G01R 33/385* (2006.01)
(Continued)

(52) U.S. Cl.
CPC .......... *G01R 33/3852* (2013.01); *A61B 5/055* (2013.01); *G01R 33/36* (2013.01);
(Continued)

(58) Field of Classification Search
CPC .. G01R 33/3852; G01R 33/543; G01R 33/36; G01R 33/561; G01R 33/3621; A61B 5/055
See application file for complete search history.

(56) References Cited

U.S. PATENT DOCUMENTS 5,672,969 A * 9/1997 Zhou ................ G01R 33/56572
324/309
6,317,619 B1 * 11/2001 Boernert .............. G01R 33/341
324/307
(Continued)

FOREIGN PATENT DOCUMENTS

JP    1033503    10/1998

OTHER PUBLICATIONS

International Search Report in PCT/JP2014/078885.
(Continued)

*Primary Examiner* — Tung X Nguyen
*Assistant Examiner* — Dominic Hawkins
(74) *Attorney, Agent, or Firm* — Cooper & Dunham LLP

(57) ABSTRACT

In order to obtain highly accurate images with a high SNR without extending measurement time or increasing hardware costs and software processing costs, the present invention narrows a dynamic range (amplitude) of an NMR signal to be received by a reception coil (reception NMR signal) in an MRI apparatus. In order to narrow the amplitude of the reception NMR signal, according to the position of an imaging region, a peak position of the reception NMR signal is shifted from the said position in the present embodiment. The shift is achieved by applying frequency encoding gradient magnetic field pulses whose application amount in the time direction is different according to the position. This is realized by a plurality of gradient magnetic field generating systems that can be driven independently.

11 Claims, 13 Drawing Sheets

(51) Int. Cl.
   *A61B 5/055* (2006.01)
   *G01R 33/561* (2006.01)
   *G01R 33/54* (2006.01)
(52) U.S. Cl.
   CPC ......... *G01R 33/543* (2013.01); *G01R 33/561* (2013.01); *G01R 33/3621* (2013.01)

(56) References Cited

U.S. PATENT DOCUMENTS

| | | | | |
|---|---|---|---|---|
| 2002/0175683 | A1* | 11/2002 | Mertelmeier | G01R 33/5611 324/314 |
| 2005/0242269 | A1* | 11/2005 | Hayashi | A61B 6/14 250/208.1 |
| 2007/0035302 | A1* | 2/2007 | Ikedo | G01R 33/56563 324/320 |
| 2008/0081986 | A1* | 4/2008 | Slavin | A61B 5/055 600/410 |
| 2010/0308826 | A1* | 12/2010 | Saes | G01R 33/3614 324/309 |
| 2011/0074416 | A1* | 3/2011 | Yamashita | A61B 5/055 324/309 |
| 2012/0169339 | A1* | 7/2012 | Kunugi | G01R 33/56509 324/309 |
| 2013/0009641 | A1* | 1/2013 | Hori | G01R 33/3852 324/309 |
| 2013/0069648 | A1* | 3/2013 | Grodzki | G01R 33/56 324/309 |
| 2013/0222512 | A1* | 8/2013 | Onishi | H03K 5/01 347/224 |
| 2013/0285664 | A1* | 10/2013 | Scheel | G01R 33/3852 324/319 |
| 2014/0111204 | A1* | 4/2014 | Wu | A61B 5/055 324/309 |

OTHER PUBLICATIONS

Davies et al., "Calibration of gradient propagation delays for accurate two-dimensional RF pulses," Proc. Intl. Soc. Mag. Reson. Med. 11, 2004, #2189.

\* cited by examiner

FIG.10
(a) 801
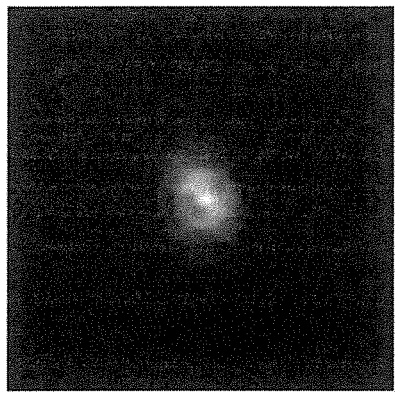
(b) 802
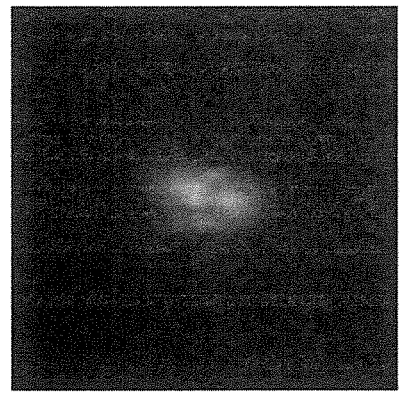
(c) 803
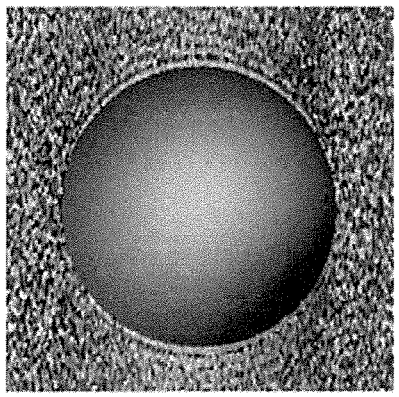
(d) 804
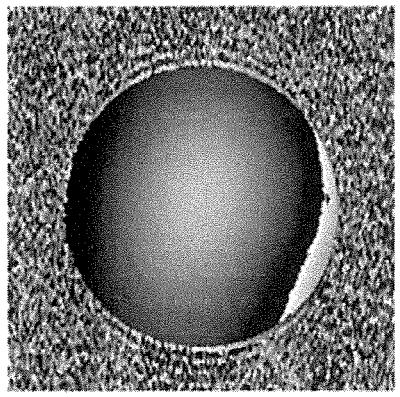
(e) 805
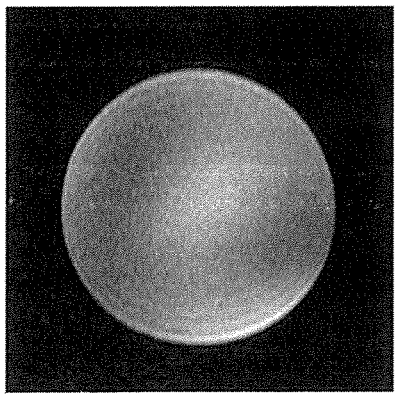
(f) 806
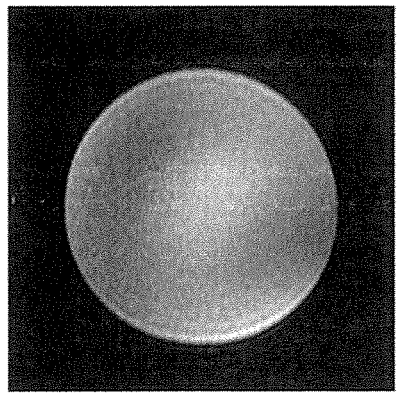

MAGNETIC RESONANCE IMAGING APPARATUS

TECHNICAL FIELD

The present invention relates to a magnetic resonance imaging (hereinafter, referred to as MRI) technique for measuring nuclear magnetic resonance signals (hereinafter, referred to as NMR signals) from hydrogen, phosphorus, etc. of an object and imaging nuclear density distribution, relaxation time distribution, etc. and, in particular, to a technique for measuring the NMR signals.

BACKGROUND ART

An MRI apparatus measures NMR signals generated by atomic nucleus spins comprising an object, particularly, human tissue to two-dimensionally or three-dimensionally image forms and functions of the head, abdomen, limbs, and the like. In imaging, the object is placed in a static magnetic field (a polarizing magnetic field Bo), a high-frequency magnetic field pulse is applied together with a slice-selective gradient magnetic field pulse in order to selectively excite a certain region, and then an excitation range is encoded to provide positional information by applying a phase encoding gradient magnetic field pulse and a frequency encoding gradient magnetic field pulse. The measured NMR signals are two-dimensionally or three-dimensionally Fourier-transformed in order to reconstruct an image.

Generally, in the MRI apparatus, by amplifying the NMR signals immediately after they are received by a reception coil, a ratio of noise to be mixed in the reception system later can be reduced relatively. At this time, gain that amplifies the NMR signals is referred to as reception gain. Since the ratio of noise to be mixed is more reduced as the reception gain is greater, an image with a high SNR can be obtained in proportion to the increase of the reception gain. Also, since a quantization error is more reduced when the NMR signals are converted into digital signals as the reception gain is greater, a highly accurate image can be obtained.

However, actually, because an A/D converter has a dynamic range limitation, a magnitude of the reception gain to be applied to the NMR signals is limited. Especially in case of a spin echo sequence, there is a timing at which phases of the NMR signals in each position are aligned, a dynamic range of an NMR signal to be received at the timing is large. Therefore, in order to correspond to the NMR signals at this timing, the reception gain of the A/D converter cannot be increased.

In order to solve this problem, there is one method of obtaining the NMR signals with a wide dynamic range by changing the reception gain to measure the NMR signals a plurality of times and synthesizing the respective measurement signals. Also, there is a method of using companding (for example, Non-patent Literature 1). In this method, analog NMR signals before AD conversion are transmitted through a non-linear amplifier (for example, a logarithmic amplifier) to perform non-linear compression processing. Then, expansion processing is performed for NMR signals after AD conversion according to the characteristics of the amplifier.

CITATION LIST

Non-Patent Literature

NPTL 1: J. Bollenbeck Et. Al., A high Performance Multi-Channel RF Receiver for Magnet Resonance Imaging Systems, Proceedings of the 13th annual meeting of ISMRM, 2005, page 860

SUMMARY OF INVENTION

Technical Problem

However, when the NMR signals are measured a plurality of times by changing the reception gain, the measurement time is extended. Also, in the method of using companding, a non-linear amplifier needs to be inserted in an analog circuit, which increases hardware costs. Additionally, the expansion processing needs to be provided also for software that performs digital processing, which increases processing costs.

The present invention is made in light of the above circumstances and has an object of obtaining highly accurate images with a high SNR without extending the measurement time or increasing the hardware costs and the software processing costs.

Solution to Problem

The present invention narrows a dynamic range (amplitude) of an NMR signal to be received by a reception coil (reception NMR signal) in an MRI apparatus. In order to narrow the amplitude of the reception NMR signal, in the present embodiment, according to the position of an imaging region, a peak position of the NMR signal is shifted from the said position. This shift is achieved by applying frequency encoding gradient magnetic field pulses whose waveforms are different according to the position. This can be achieved by a plurality of gradient magnetic field generating systems that can be driven independently.

In other words, a gradient magnetic field application unit is provided that applies two or more gradient magnetic field pulses composed of waveforms different from each other according to the spatial position on the gradient magnetic field application axis in an imaging region, and the gradient magnetic field application unit applies gradient magnetic field pulses with two or more different waveforms and applies gradient magnetic field pulses composed of one predetermined waveform.

Advantageous Effects of Invention

According to the present invention, because a dynamic range of an NMR signal to be measured is narrowed and reception gain for the said NMR signal can be increased, a ratio of noise superimposed in a reception system can be reduced, which also reduces a quantization error in AD conversion. Therefore, highly accurate images with a high SNR can be obtained without extending the measurement time or increasing the hardware costs and the software processing costs.

BRIEF DESCRIPTION OF DRAWINGS

FIGS. 10(a), 10(c), and 10(e) show explanatory views for explaining k-space data, a phase image, and an absolute value image to be obtained when a pair of gradient magnetic field coils is driven by shifting timings, and FIGS. 10(b), 10(d), and 10(f) show explanatory views for explaining k-space data, a phase image, and an absolute value image to be obtained when the pair of gradient magnetic field coils is driven simultaneously.

DESCRIPTION OF EMBODIMENTS

<<First Embodiment>>

Hereinafter, the first embodiment of the present invention will be described in detail according to the attached drawings. Additionally, in all the drawings of the present description, the same reference signs are used for components having the same functions, and the repeated explanations are omitted.

<Apparatus Configuration>

Figure 1:
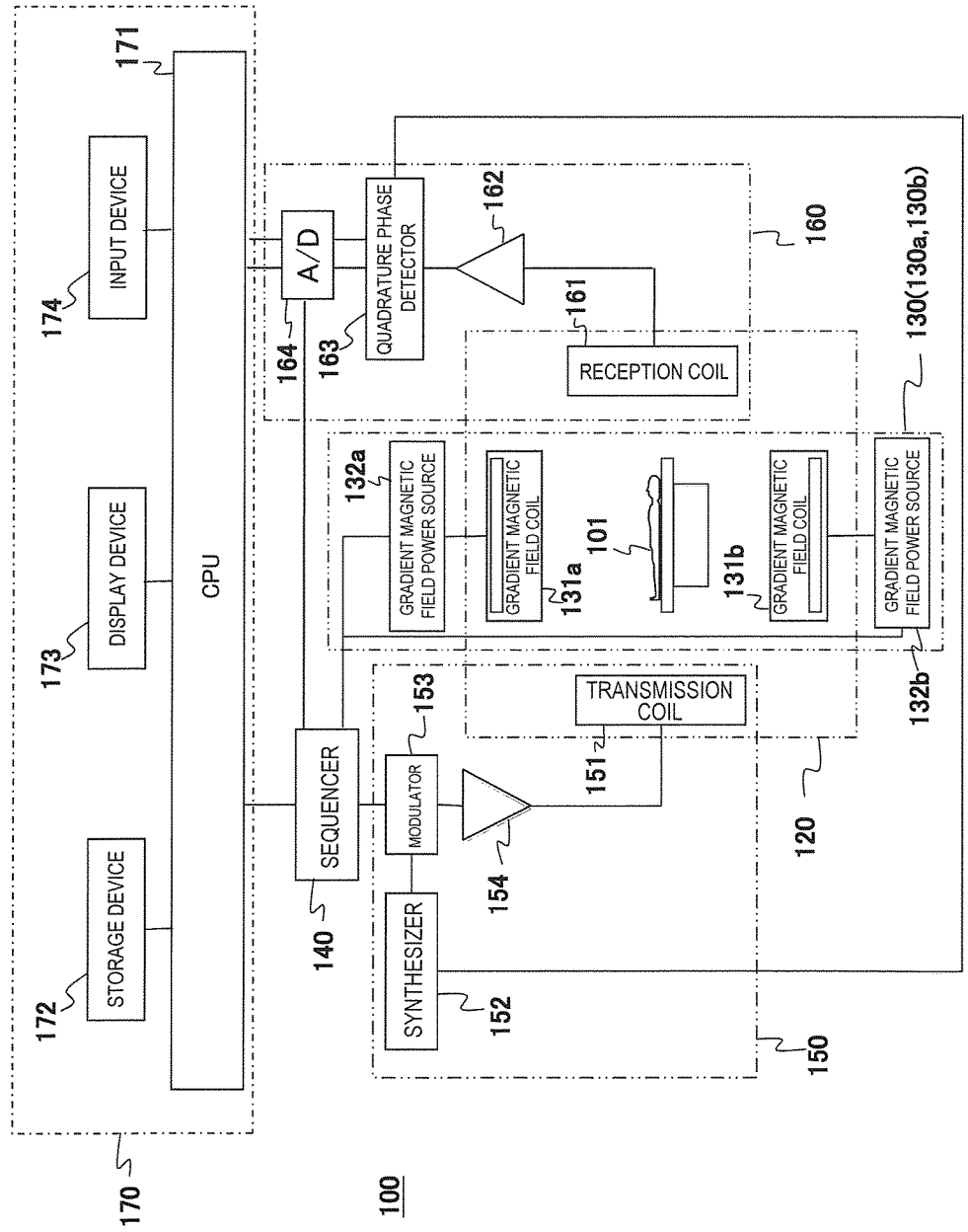
FIG. 1 is a block diagram of an MRI apparatus of a first embodiment.

First, an overview of an example of an MRI apparatus related to the present invention will be described based on FIG. 1. FIG. 1 is a block diagram showing an overall configuration of one embodiment of the MRI apparatus related to the present invention.

An MRI apparatus 100 of the present embodiment is provided with the gradient magnetic field application unit that applies two or more gradient magnetic field pulses composed of waveforms different from each other according to the spatial position on the gradient magnetic field application axis in an imaging region, and the gradient magnetic field application unit applies gradient magnetic field pulses with two or more different waveforms and applies gradient magnetic field pulses composed of one predetermined waveform in order to obtain tomographic images of an object using the NMR phenomenon. As shown in FIG. 1, the gradient magnetic field application unit comprises a static magnetic field generating system 120, a gradient magnetic field generating system 130, a high-frequency magnetic field generating system (hereinafter, referred to as a transmission system) 150, a high-frequency magnetic field detecting system (hereinafter, referred to as a reception system) 160, a control processing system 170, and a sequencer 140.

The static magnetic field generating system 120 generates a uniform static magnetic field in a direction orthogonal to the body axis of an object 101 in a space around the object 101 in case of a vertical magnetic field method and in the body axis in case of a horizontal magnetic field method and is provided with a static magnetic field generating source to be disposed around the object 101, and the static magnetic field generating source uses a permanent magnet system, a normal conducting system, or a superconducting system.

The gradient magnetic field generating system 130 comprises a pair of gradient magnetic field coils 131a and 131b generating gradient magnetic fields in the three X-, Y-, and Z-axis directions that are a coordinate system of the MRI apparatus 100 (an apparatus coordinate system) and a pair of gradient magnetic field power sources 132a and 132b driving the respective gradient magnetic field coils 131a and 131b and applies gradient magnetic fields Gx, Gy, and Gz in the three X-, Y-, and Z-axis directions by driving the gradient magnetic field power sources 132a and 132b of the respective gradient magnetic field coils 131a and 131b according to a command from a sequencer 140 to be described later.

Additionally, hereinafter, in the present embodiment, the respective gradient magnetic field coil 131a and the gradient magnetic field power source 132a are referred to as a gradient magnetic field generating system 130a, and the respective gradient magnetic field coil 131b and the gradient magnetic field power source 132b are referred to as a gradient magnetic field generating system 130b. That is, in the present embodiment, a pair of the gradient magnetic field generating systems 130a and 130b is provided in which a gradient magnetic field coil and a gradient magnetic field power source are included respectively.

During imaging, a slice plane is set for the object 101 by applying a slice gradient magnetic field pulse in a direction orthogonal to the slice surface (imaging cross section), a phase encoding gradient magnetic field pulse and a frequency encoding gradient magnetic field pulse are applied in the remaining two directions that are orthogonal to the slice surface and to each other, and then positional information in the respective directions is encoded for the NMR signals (NMR signals).

In order to generate nuclear magnetic resonance to atomic nucleus spins of atoms comprising human tissue of the object 101, the transmission system 150 irradiates a high-frequency magnetic field pulse (hereinafter, referred to as "RF pulse") to the object 101 and provided with a high-frequency oscillator (synthesizer) 152, a modulator 153, a high-frequency amplifier 154, and a high-frequency coil on the transmission side (transmission coil) 151. The high-frequency oscillator 152 generates and outputs an RF pulse. The modulator 153 amplitude-modulates the output RF pulse at a timing of a command from the sequencer 140, and the high-frequency amplifier 154 amplifies the amplitude-modulated RF pulse and supplies it to the transmission coil 151 disposed in the vicinity of the object 101. The transmission coil 151 irradiates the supplied RF pulse to the object 101.

The reception system 160 detects NMR signals to be emitted by nuclear magnetic resonance of atomic nucleus spins comprising human tissue of the object 101 and comprises a high-frequency coil on the reception side (reception coil) 161, a signal amplifier 162, a quadrature phase detector 163, and an A/D converter 164. The reception coil 161 is disposed in the vicinity of the object 101 to detect response NMR signals of the object 101 that are induced by electromagnetic waves irradiated from the transmission coil 151. The detected NMR signals are amplified by the signal amplifier 162, divided into two system signals by the quadrature phase detector 163 at a timing of a command from the sequencer 140, converted into a digital amount by the A/D converter 164 respectively, and then sent to the control processing system 170. In the present embodiment, a case of using the reception coil 161 with a plurality of channels will be described as an example.

The sequencer 140 applies an RF pulse and a gradient magnetic field pulse according to the command from the control processing system 170 and controls the respective portions so as to receive the generated NMR signals. Specifically, according to the command from the control processing system 170, various commands required for collecting cross-sectional image data of the object 101 are sent to the transmission system 150, the gradient magnetic field generating system 130, and the reception system 160.

The control processing system 170 controls the MRI apparatus 100 entirely, performs calculations such as various data processes, displays and saves the processing results, and the like. The control processing system 170 comprises a CPU 171, a storage device 172, a display device 173, and an input device 174. The storage device 172 is composed of an internal storage device such as a hard disk and external storage devices such as an external hard disk, an optical disk, and a magnetic disk. The display device 173 is a display device such as a CRT display and a liquid crystal display. The input device 174 is an interface for inputting various control information of the MRI apparatus 100 and control information of processes to be performed in the control processing system 170 and includes a trackball or a mouse and a keyboard for example. The input device 174 is disposed in the vicinity of the display device 173. An operator watches the display device 173 and inputs commands and data required for various processes of the MRI apparatus 100 interactively through the input device 174.

The CPU 171 performs operation control of the MRI apparatus 100 and various processes of the control processing system 170 such as various data processes by executing programs previously stored in the storage device 172 according to the command input by the operator. The above command to the sequencer 140 is made according to the pulse sequence previously stored in the storage device 172. Also, when data from the reception system 160 is input to the control processing system 170, the CPU 171 executes a signal process, an image reconstruction process, and the like, and the resultant tomographic images of the object 101 are displayed on the display device 173 and stored in the storage device 172.

The transmission coil 151 and the gradient magnetic field coils 131 are installed opposite to the object 101 in case of the vertical magnetic field method or installed so as to surround the object 101 in case of the horizontal magnetic field method in a static magnetic field space of the static magnetic field generating system 120 where the object 101 is inserted. Also, the reception coil 161 is installed opposite to the object 101 or so as to surround the object 101.

Currently, a clinically prevalent isotope to be imaged by an MRI apparatus is a hydrogen atomic nucleus (proton) that is a main c component material of the object 101. In the MRI apparatus 100, forms and functions of the head, abdomen, limbs, and the like of a human are imaged two-dimensionally or three-dimensionally by converting information about spatial distribution of proton density and spatial distribution of excitation state relaxation time into an image.

Hereinafter, description will be made mainly for operations of the MRI apparatus 100 of the present embodiment having the above configuration, in particular, an operation when gradient magnetic field pulses are applied by the control processing system 170, the sequencer 140, and the gradient magnetic field generating system 130.

In the present embodiment, the peak is reduced without changing an information amount of NMR signals to be received by the reception coil 161 (reception NMR signals) in order to provide reception gain as large as possible to the received NMR signals. That is, amplitudes of the reception NMR signals are narrowed.

The reception NMR signals are made by synthesizing NMR signals from the respective spatial positions (the respective pixels) in an imaging region. Therefore, in order to narrow amplitudes of the reception NMR signals, the peak positions (peak timings) of the NMR signals from the respective pixels in the imaging region are shifted according to the pixels in the present embodiment. Hence, the peaks of the reception NMR signals that are synthesis of the NMR signals from the respective pixels, which narrows the amplitudes.

In the present embodiment, shifting the peak positions of the NMR signals is achieved by changing gradient magnetic field pulse waveforms according to the spatial position (pixel) before the application in the imaging region (field of view). Additionally, the gradient magnetic field pulse waveforms are determined by a variation mode in the time direction of the gradient magnetic field strength. In the present embodiment, changing the forms of the application pulses is achieved by providing the same waveform signals to a pair of the gradient magnetic field generating systems 130a and 130b at different timings.

The respective gradient magnetic field generating systems 130a and 130b apply gradient magnetic field pulses according to the timing of obtaining the waveform signal.

<Gradient Magnetic Field Application Unit>

In the present embodiment, as described above, the control processing system 170, the sequencer 140, and the gradient magnetic field generating system 130 realize a gradient magnetic field application unit 200 that applies gradient magnetic field pulses so as to have different waveforms according to the spatial position on the gradient magnetic field application axis in an imaging region. The waveforms are determined by a variation amount in the time direction of magnetic field strength per unit distance as described above.

Figure 2:
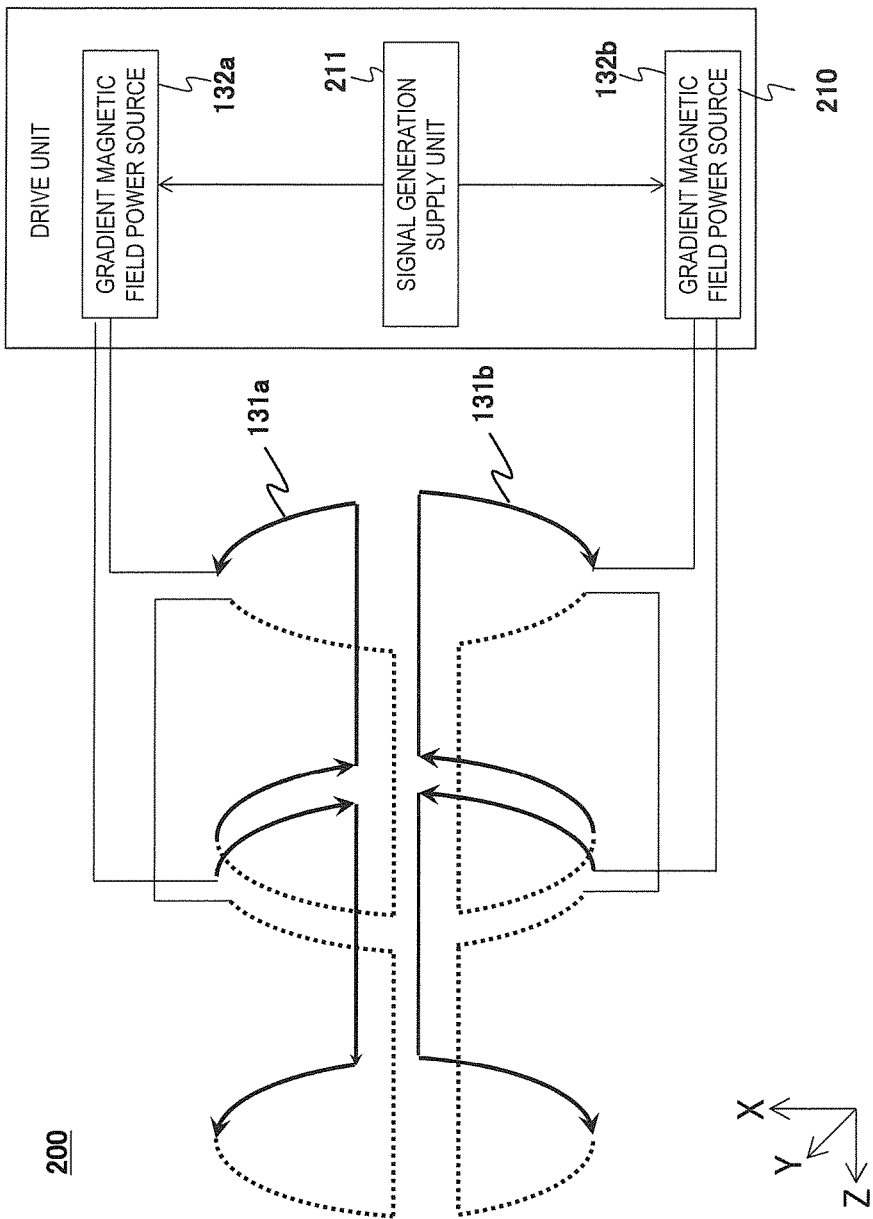
FIG. 2 is a block diagram of a gradient magnetic field application unit of the first embodiment.

FIG. 2 is a view for explaining the configuration of the gradient magnetic field application unit 200 of the present embodiment. Here, only the X-axis direction is shown as an example. For each of a pair of gradient magnetic field coils and a pair of the gradient magnetic field coils 131a and 131b, the gradient magnetic field application unit 200 of the present embodiment is provided with a drive unit 210 that supplies driving electric currents whose time integration values to an arbitrary time are different.

The drive unit 210 comprises a signal generation supply unit 211 and a pair of the gradient magnetic field power sources 132a and 132b as shown in the present figure. The signal generation supply unit 211 generates waveform signals instructing to apply gradient magnetic field pulses according to the predetermined pulse sequence and supplies the said waveform signals to each of the gradient magnetic field power sources 132a and 132b so that integration values to an arbitrary time are different. The pair of the gradient magnetic field power sources 132a and 132b is connected to the pair of the gradient magnetic field coils 131a and 131b respectively to supply driving electric currents to the said gradient magnetic field coils 131a and 131b according to the supplied waveform signals.

In the present embodiment, the signal generation supply unit 211 supplies one generated waveform signal to the pair of the gradient magnetic field power sources 132a and 132b respectively at different timings. Hence, in the present embodiment, the driving electric currents are supplied from the pair of the gradient magnetic field power sources 132a and 132b so as to have a period when only one of the pair of the gradient magnetic field coils 131a and 131b is driven.

Additionally, the present embodiment aims to shift peak positions of NMR signals. The signal generation supply unit 211 of the present embodiment supplies waveform signals to the pair of the gradient magnetic field power sources 132a and 132b at different timings only when a frequency encoding gradient magnetic field pulse is applied.

The signal generation supply unit 211 is realized by the control processing system 170 and the sequencer 140. Specifically, the CPU 171 loads a program previously stored in the storage device 172 or the like in a memory before the execution and provides a command to the sequencer 140, which realizes the signal generation supply unit 211. The generated waveform signals are supplied to the gradient magnetic field power sources 132a and 132b by the sequencer 140.

Additionally, the signal generation supply unit 211 may not be exclusive to the gradient magnetic field pulse application. The signal generation supply unit 211 may also generate waveform signals instructing to apply all the pulses in a pulse sequence including an RF pulse and supply them to each application unit.

When the same waveform signals are provided to the pair of the gradient magnetic field coils 131a and 131b at different timings, different-shaped gradient magnetic field pulses are applied in the time direction in each spatial position on the gradient magnetic field application axis. When the different-shaped gradient magnetic field pulses are applied in the time direction in each spatial position on the gradient magnetic field application axis, amplitudes of reception NMR signals are narrowed. These will be described using drawings. Here, the X-axis direction is taken as an example.

Figure 3:
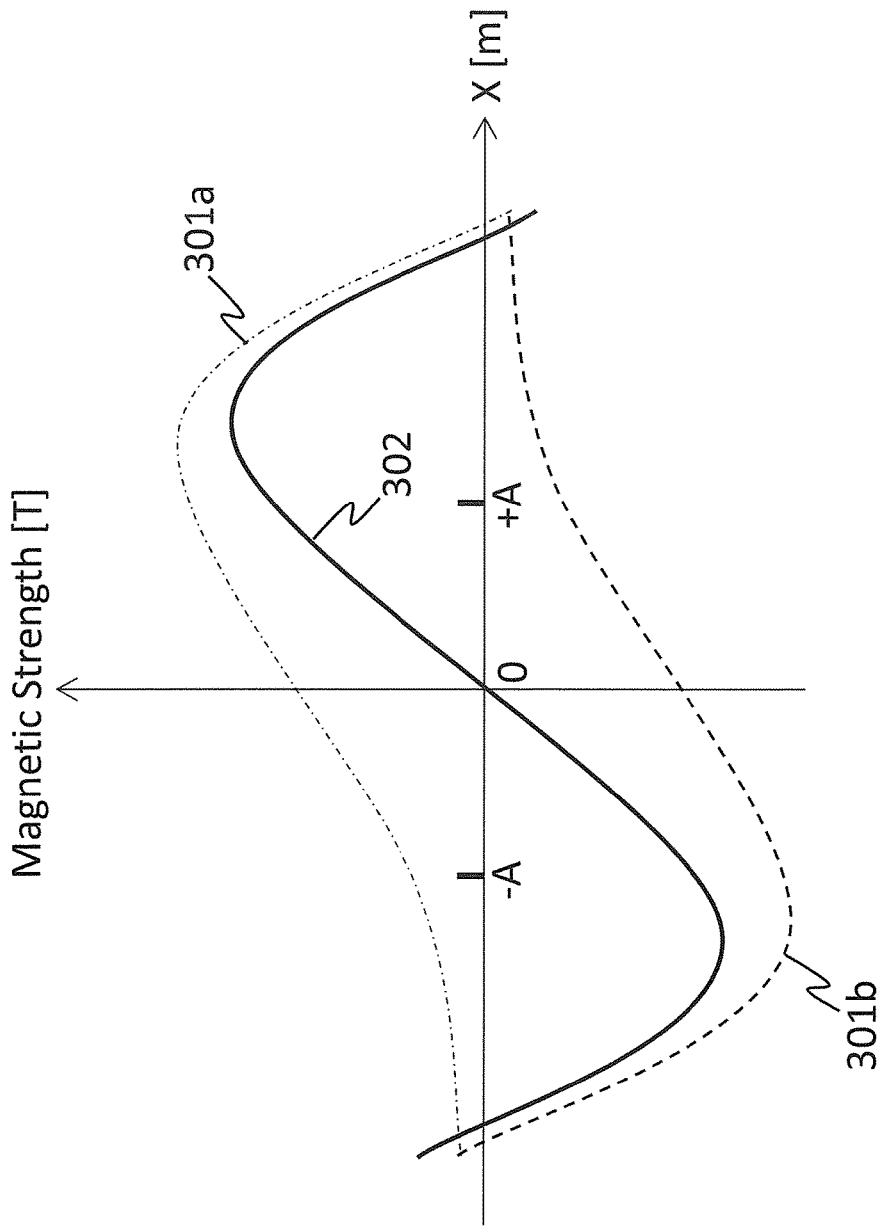
FIG. 3 is an explanatory view for explaining a magnetic field distribution when a pair of gradient magnetic field coils is driven with the same amount of an electric current simultaneously.

First, FIG. 3 shows a magnetic field to be applied by the respective gradient magnetic field coils 131a and 131b when the same waveform signals are simultaneously provided to the gradient magnetic field power sources 132a and 132b. In the present figure, the horizontal axis shows a position X [m] in the X-axis direction, and the vertical axis shows a magnetic field strength (Magnetic Strength [T]).

When the same waveform signals are simultaneously received through the sequencer 140 from the signal generation supply unit 211, the gradient magnetic field power sources 132a and 132b simultaneously apply the same amount of electric current to the respective gradient magnetic field coils 131a and 131b. Consequently, a magnetic field distribution 301a is obtained by the gradient magnetic field coil 131a, and a magnetic field distribution 301b is obtained by the gradient magnetic field coil 131b. Therefore, both the magnetic field distributions are synthesized, and a magnetic field distribution 302 is obtained.

Figure 4:
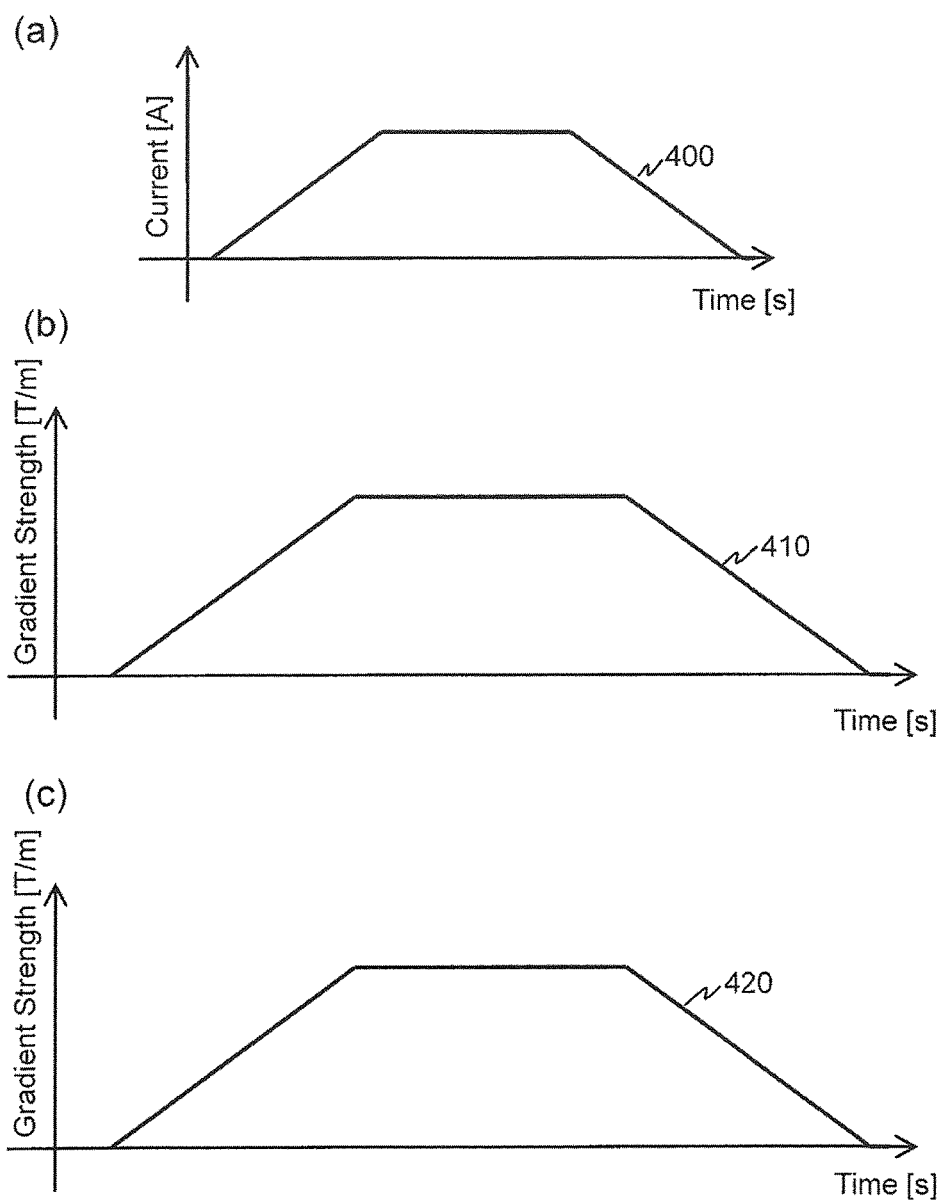
FIG. 4(a) shows an explanatory view for explaining a waveform of a driving electric current to be supplied to a gradient magnetic field coil.
FIGS. 4(b) and 4(c) show explanatory views for explaining the respective gradient magnetic field pulse waveforms at positions +A and −A.
Figure 5:
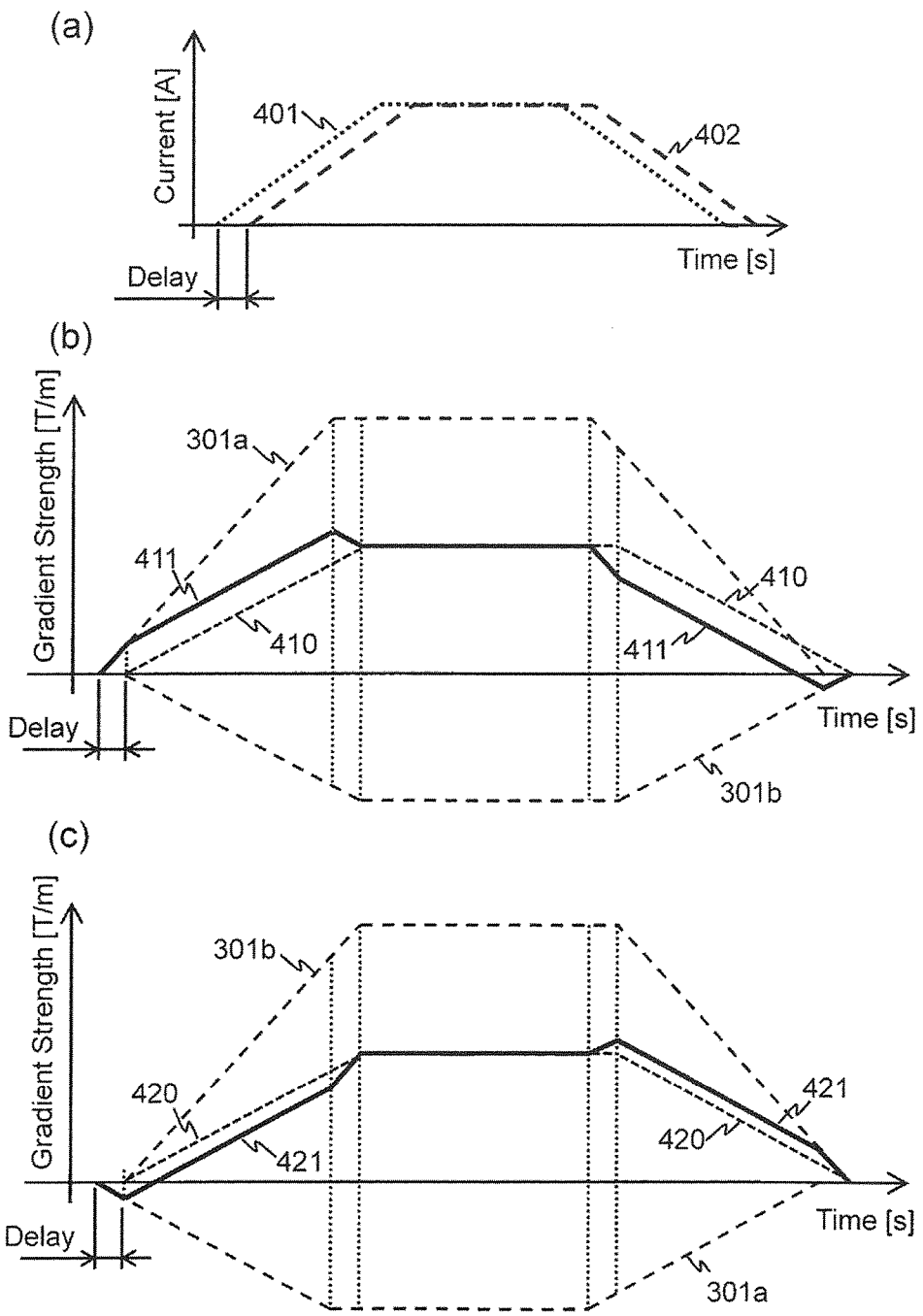
FIG. 5(a) shows an explanatory view for explaining driving electric currents to be supplied to a pair of gradient magnetic field coils at different timings.
FIGS. 5(b) and 5(c) show explanatory views for explaining gradient magnetic field pulse waveforms at the positions +A and −A.
Figure 6:
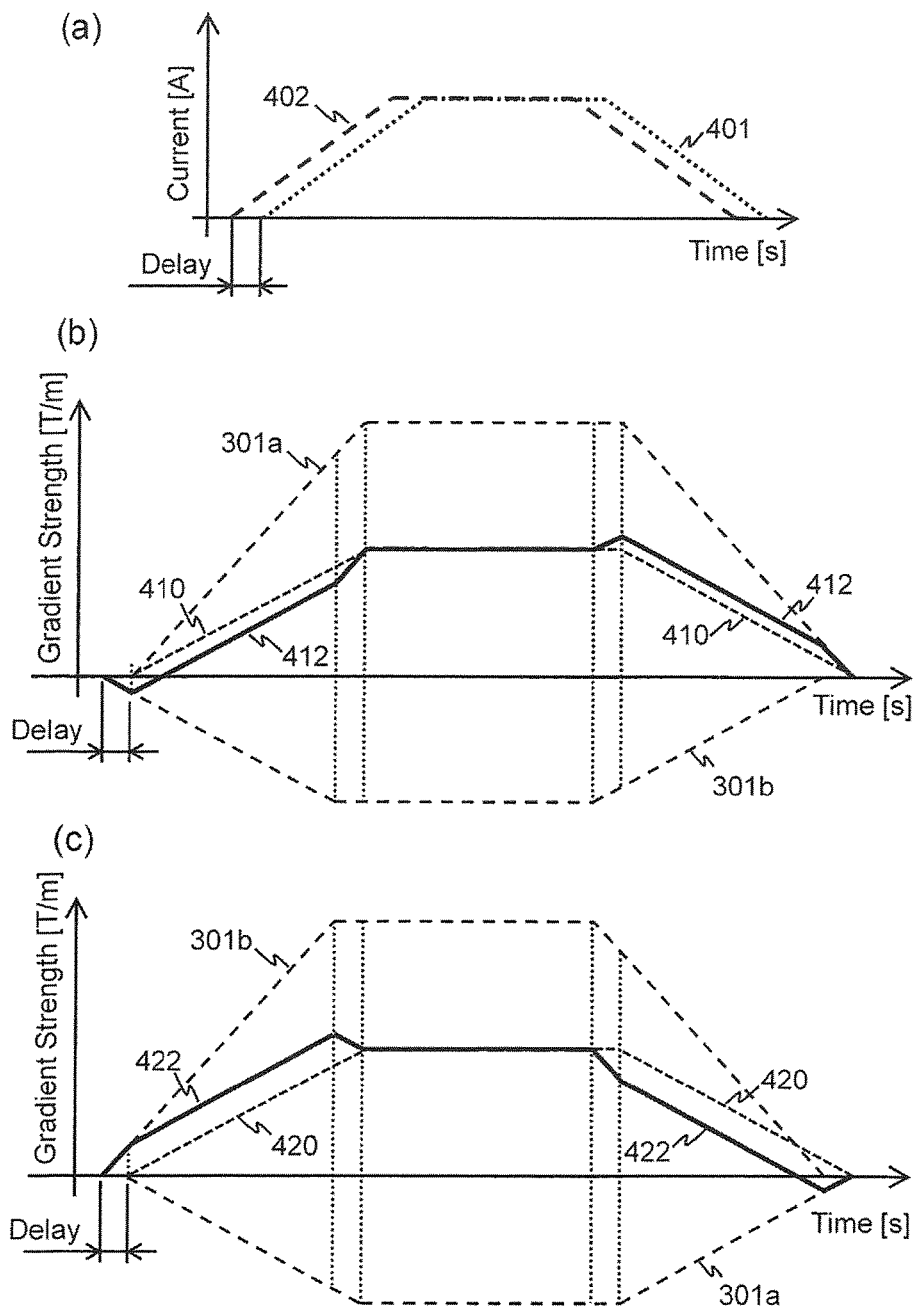
FIG. 6(a) shows an explanatory view for explaining driving electric currents to be supplied to a pair of gradient magnetic field coils at different timings.
FIGS. 6(b) and 6(c) show explanatory views for explaining gradient magnetic field pulse waveforms at the positions +A and −A.

FIGS. 4(a) to 4(c) show a driving electric current 400 to be supplied from the respective gradient magnetic field power sources 132a and 132b to the respective gradient magnetic field coils 131a and 131b and waveforms of gradient magnetic field pulses to be applied to an arbitrary position on the X axis in a case where waveform signals to be supplied from the signal generation supply unit 211 are trapezoidal waves. In FIG. 4(a), the horizontal axis shows a time (Time [s]), and the vertical axis shows a current (Current [A]). In FIGS. 4(b) and 4(c), the horizontal axes show a time (Time [s]), and the vertical axes show a gradient magnetic field pulse strength (Gradient Strength [T/m]) normalized by distance. Shown here are a gradient magnetic field pulse waveform 410 to be applied to a position +A and a gradient magnetic field pulse waveform 420 to be applied to a position −A as an arbitrary position. Also, FIG. 4(c) shows an inverted polarity.

When the same waveform signals are simultaneously supplied to the gradient magnetic field power sources 132a and 132b, the driving electric current 400 shown in FIG. 4(a) is supplied to the gradient magnetic field coils 131a and 131b. According to this, the same-shaped gradient magnetic field pulses are simultaneously generated from the respective gradient magnetic field coils 131a and 131b. Therefore, as shown in FIGS. 4(b) and 4(c), the gradient magnetic field pulses 410 and 420 in which these gradient magnetic field pulses were synthesized are applied respectively to the positions +A and −A. As shown in the present figure, these gradient magnetic field pulses have approximately same shapes.

Here, when waveform signals of trapezoidal waves with the same shape are received from the signal generation supply unit 211 at different timings, FIGS. 5(a) to 6(c) show electric currents to be supplied to the respective gradient magnetic field coils 131a and 131b by the gradient magnetic field power sources 132a and 132b and waveforms of gradient magnetic field pulses to be supplied to the positions +A and −A respectively. Additionally, the waveform of the gradient magnetic field pulse to be applied to the position −A is shown by inverting the polarity of the vertical axis.

FIG. 5(a) shows driving electric currents 401 and 402 to be supplied to the gradient magnetic field coils 131a and 131b respectively. Gradient magnetic field pulses 411 and 421 shown in FIGS. 5(b) and 5(c) are waveforms of the gradient magnetic field pulses to be applied to the positions +A and −A respectively in a case where a timing of supplying the driving electric current 401 to the gradient magnetic field coil 131a is set earlier than that of supplying the driving electric current 402 to the gradient magnetic field coil 131b by a time difference Delay. Additionally, similarly to FIG. 3, 301a and 301b are a magnetic field distribution to be obtained by the gradient magnetic field coil 131a and the magnetic field distribution 301b to be obtained by the gradient magnetic field coil 131b respectively.

When the same waveform signals are supplied to the gradient magnetic field power sources 132a and 132b by shifting by the time difference Delay, the driving electric currents 401 and 402 shown in FIG. 5(a) are supplied to the gradient magnetic field coils 131a and 131b respectively.

As shown in FIG. 5(b), the electric current 402 is not supplied to the gradient magnetic field coil 131b generating a reverse magnetic field until the time difference Delay after the electric current 401 is supplied to the gradient magnetic field coil 131a. Therefore, a sudden change in the magnetic field strength occurs in the start portion of the rising portion of a gradient magnetic field pulse only during the time difference Delay.

When the electric current 402 is supplied also to the gradient magnetic field coil 131b after the time difference Delay, a gradient magnetic field in which magnetic fields generated by both the gradient magnetic field coils are synthesized is changed at the same inclination as 410. This is because change rates of both the magnetic fields are the same as a case without Delay during this period.

Then, a magnetic field to be generated by the gradient magnetic field coil 131a enters a plateau portion before that to be generated by the gradient magnetic field pulse 131b. Therefore, a sudden change in magnetic field strength occurs in the opposite direction to the start of the rising portion of the gradient magnetic field pulse at the end of the rising portion of the gradient magnetic field pulse.

This is similar also at the falling portion of the gradient magnetic field pulse.

The sudden changes in magnetic field strength to occur at the start and the end of the rising and falling portions of the gradient magnetic field pulse occurs with the same polarity in the positions +A and −A. However, the polarities of the magnetic field changes to be generated by the gradient magnetic field pulse are in the opposite directions in the positions +A and −A. Therefore, waveforms of the gradient magnetic fields to be generated in each position of +A and −A have different shapes from each other as shown in FIGS. 5(a) and 5(b).

Also, FIG. 6(a) shows the driving electric currents 401 and 402 to be supplied to the respective gradient magnetic field coils 131a and 131b. FIGS. 6(b) and 6(c) respectively show waveforms of the gradient magnetic field pulses to be applied to the positions +A and −A in a case where a timing of supplying the driving electric current 401 to the gradient magnetic field coil 131a is set later than that of supplying to the gradient magnetic field coil 131b by the time difference Delay. Also, similarly to FIG. 3, 301a and 301b are a magnetic field distribution to be obtained by the gradient magnetic field coil 131a and the magnetic field distribution 301b to be obtained by the gradient magnetic field coil 131b respectively.

When the same waveform signals are supplied to the gradient magnetic field power sources 132a and 132b by shifting by the time difference Delay, the driving electric currents 401 and 402 shown in FIG. 6(a) are supplied to the gradient magnetic field coils 131a and 131b respectively. According to this, magnetic fields are generated according to the supplied time from each of the gradient magnetic field coils 131a and 131b. Therefore, as shown in FIGS. 6(b) and 6(c), gradient magnetic field pulses 412 and 422 in which these gradient magnetic field pulses were synthesized in consideration of the shift of the application time are applied to the positions +A and −A respectively. Thus, different-shaped gradient magnetic field pulses are applied according to the position by providing the time difference Delay.

FIG. 7(a) show waveforms of gradient magnetic field pulses to be applied to different four positions (+A1, +A2, +A3, and +A4: +A1>+A2>+A3>+A4) in the X-axis positive direction when the driving electric currents 401 and 402 are supplied to the gradient magnetic field coils 131a and 131b as shown in FIG. 5(a). In the present figure, the horizontal axis shows a Time [s], and the vertical axis shows a gradient magnetic field pulse strength (Gradient Strength [T]). Also, 502, 503, 504, and 505 are waveforms of the gradient magnetic field pulses to be applied to the positions +A1, +A2, +A3, and +A4 respectively.

In the present figure, gaps 521 are generated because there are periods when magnetic fields suddenly change. As described above, this is because there is a period (time difference Delay) when one of the other gradient magnetic field coil 131a starts driving earlier and the other gradient magnetic field coil 131b is not driven. The gaps 521 have the same size in any position.

FIG. 7(b) shows waveforms of gradient magnetic field pulses when the gradient magnetic field pulse strengths of each position shown in FIG. 7(a) are divided, i.e. normalized by distance. In the present figure, the horizontal axis shows a Time [s], and the vertical axis shows a gradient magnetic field pulse strength (Gradient Strength [Tim]) normalized by distance. Additionally, 501 is a waveform of the gradient magnetic field pulse in case of supplying an electric current at the same timing. As described above, because the gaps 521 have the same size in any position, a gap 521 portion is more reduced when the gap position is distant from the magnetic field center by dividing by the distance. Therefore, the gradient magnetic field pulse waveform varies according to the position.

Thus, waveforms of the gradient magnetic field pulses to be applied from the gradient magnetic field coils 131a and 131b vary according to the position by providing a time difference Delay and supplying waveform signals to the gradient magnetic field power sources 132a and 132b at different timings even when the waveform signals are the same. The shape variation appears in the rising and falling portions of trapezoidal waves. That is, when a pair of the gradient magnetic field coils 131a and 131b is driven at different timings, gradient magnetic field pulses, whose waveforms are different according to the position, are applied. The gradient magnetic field pulses to be applied have different shapes in the rising and falling portions of the trapezoidal waves.

A peak position of an NMR signal is determined by an integration value in the time direction of an application amount of frequency encoding gradient magnetic field pulses. For example, the NMR signal peak position is where an integration value of the frequency encoding gradient magnetic field pulse of the positive polarity and that of the negative polarity correspond each other. Therefore, waveforms of the frequency encoding gradient magnetic field pulses to be applied are different, and peak positions are also different when temporal changes of the application amounts are different.

Therefore, for example, when waveform signals are supplied to each of a pair of the gradient magnetic field coils 131a and 131b pair at different timings in case of applying frequency encoding gradient magnetic field pulses in a spin echo sequence, frequency encoding gradient magnetic field pulses, whose waveforms are different according to the position, are applied. Consequently, according to the position, a timing when phases of NMR signals to be measured are aligned change, which provides no case where all the NMR signals become the same phase simultaneously. This results in that a synthesized NMR signal to be measured does not have a single peak.

Thus, the signal generation supply unit 211 of the present embodiment supplies generated signals without a time difference Delay to one of the pair of the gradient magnetic field power sources 132a and 132b as well as the generated signals to the other after providing a predetermined time difference Delay. Next, the time difference Delay in this case will be described.

Figure 7:
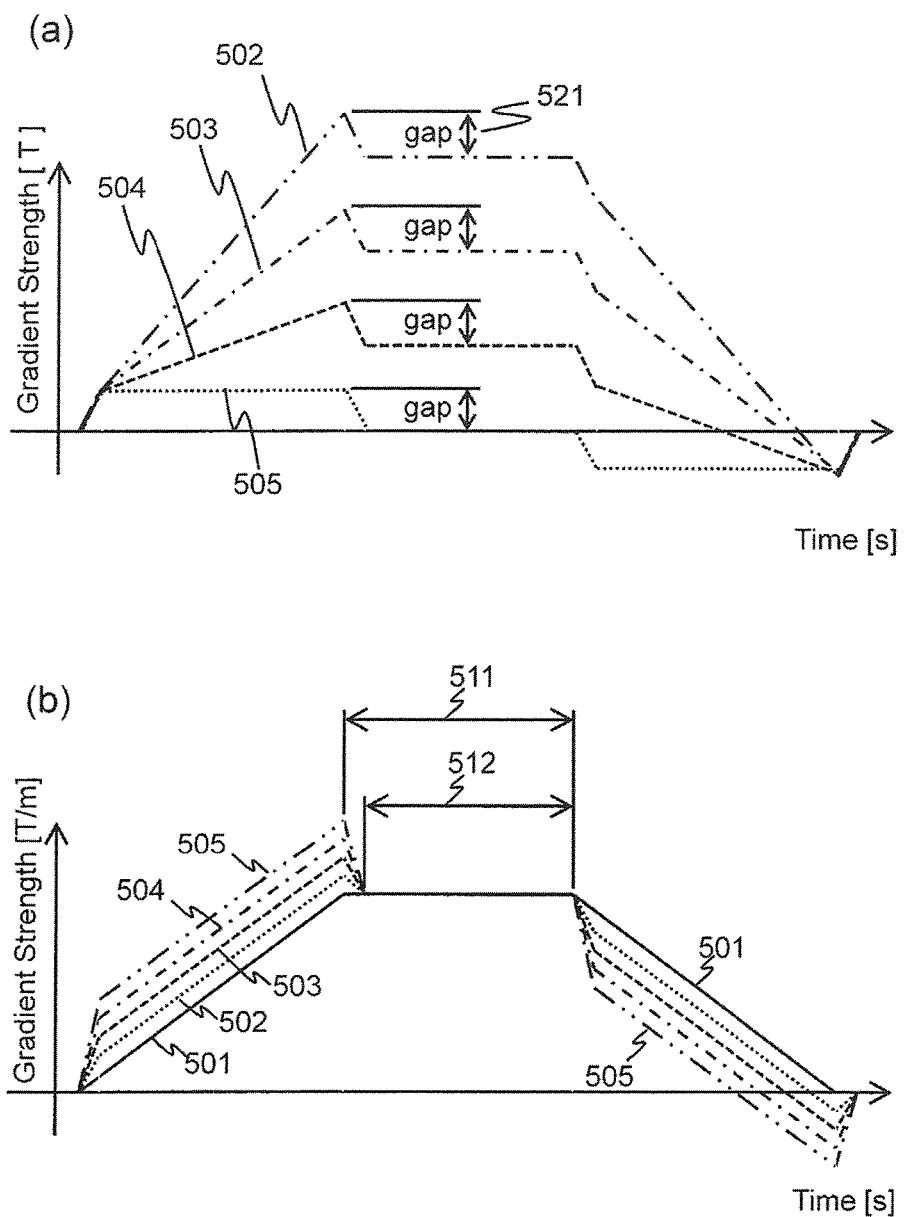
FIGS. 7(a) and 7(b) are explanatory views for explaining gradient magnetic field pulse waveforms to be applied to each position in the first embodiment.

As shown in FIG. 7, compared to a plateau portion 511 in case of applying gradient magnetic field pulses simultaneously from the two gradient magnetic field coils 131a and 131b, a time of a plateau portion 512 in case of a different application timing is shortened. The shortening intervals are determined by an application timing difference (shift time) according to the time difference Delay.

Additionally, NMR signals obtained in a region where a gradient magnetic field pulse waveform changes (other than a rising portion, a falling portion, and a plateau portion) need to be arranged in k-space after decomposing the signals for each position, which increases processing costs. In order to prevent this processing cost increase, it is desirable to obtain the NMR signals only in the plateau portion 512 where only the shift time was shortened.

<Time Difference>

A dynamic range of a reception NMR signal varies depending on the shift time between timings when the two gradient magnetic field coils 131a and 131b apply frequency encoding gradient magnetic field pulses. Although this depends on the imaging object or the pulse sequence, the dynamic range of the reception NMR signal becomes narrower as the shift time (time difference Delay) is longer as a tendency.

However, the time difference Delay of the application timing affects a time of the plateau 512 of the frequency encoding gradient magnetic field pulses shown in FIG. 7. Also, the longer the time difference Delay, the greater the difference becomes between application amounts of the frequency encoding gradient magnetic field pulses according to the position. Therefore, the more distant the position where NMR signals are generated from the gradient magnetic field center, the more the NMR signals move to the outside of a time range to obtain signals, which results in a low spatial resolution of an image. Hence, it is not desirable that an unnecessarily long time difference Delay is provided.

Shapes of the NMR signals vary according to measurement conditions, imaging objects, and the like. However, generally, only signals values in the vicinity of the k-space center are extremely high. Therefore, shift time between timings for applying frequency encoding gradient magnetic field pulses, i.e. a time difference Delay to supply waveform signals is determined so as to spread signals in the vicinity of the k-space center with high signal values.

However, the time difference Delay is determined in a range where application time of the frequency encoding gradient magnetic field pulses can be extended in a pattern of pulse sequences to be used for imaging.

Hereinafter, the time difference Delay will be described using a specific pulse sequence example. Here, the description will be made by taking a case of using a gradient echo sequence whose number of slices is one, as an example.

Figure 8:
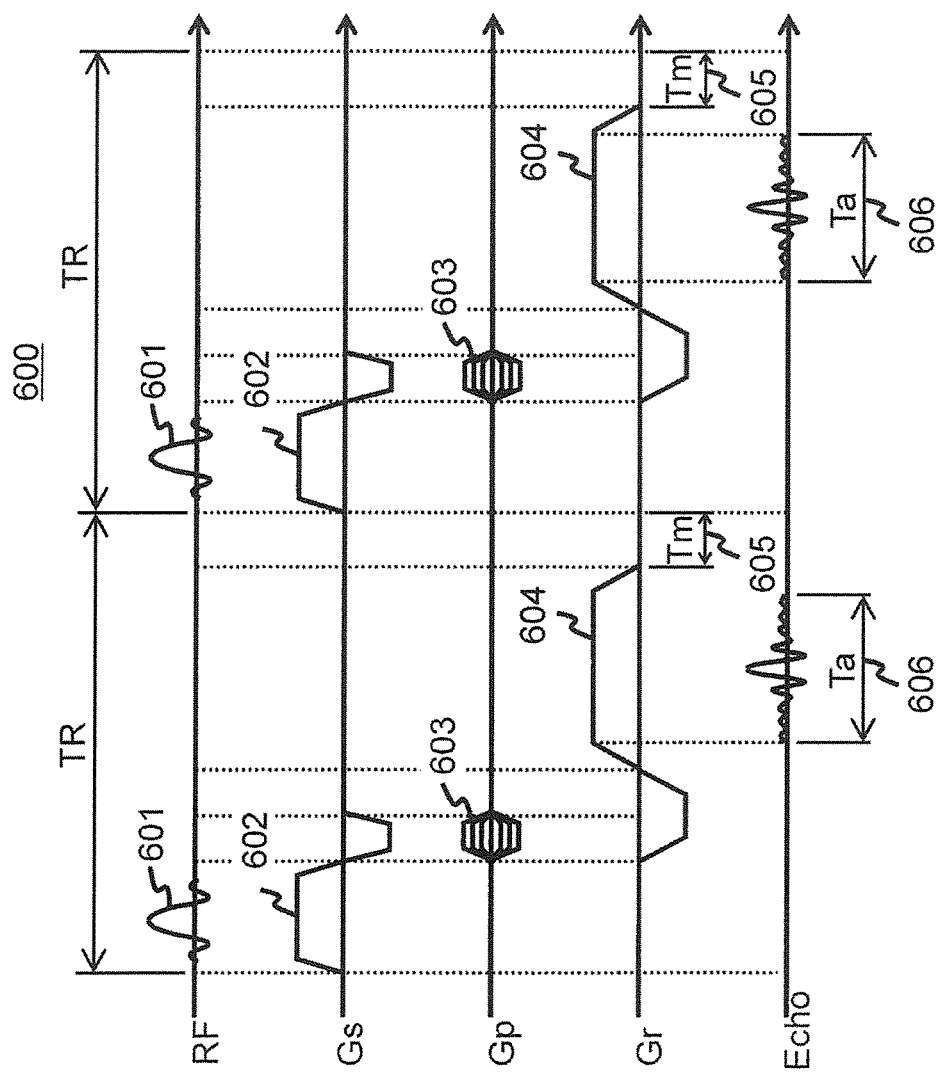
FIG. 8 is a sequence diagram of pulse sequences in a gradient echo sequence of the first embodiment.

FIG. 8 shows an example of a pulse sequence 600 of the gradient echo sequence whose number of slices is one. Additionally, some pulses are omitted in order to simplify the description.

In the pulse sequence 600, RF pulses 601, slice selection gradient magnetic field pulses 602, phase encoding gradient magnetic field pulses 603, and frequency encoding gradient magnetic field pulses 604 are applied. A Tm 605 is spare time between repetition times TR, i.e. a difference between time to apply all the pulses in the pulse sequence (execution time) and the repetition times TR. Also, a Ta 606 is obtaining time of NMR signals (echo signals). The Ta 606 shows time of a plateau portion of the frequency encoding gradient magnetic field pulse 604.

When the present embodiment is applied to the pulse sequence 600, a timing of applying the frequency encoding gradient magnetic field pulses 604 from the two gradient magnetic field coils 131a and 131b is shifted within a range of the spare time Tim 605. In order to meet the conditions, a shift time (time difference Delay) is calculated according to the following formula (1).

$$Delay \leq Tm/2 \qquad (1)$$

Also, the obtaining time Ta 606 of the NMR signals are not changed at this time. That is, a time Ta' of the plateaus portion of the frequency encoding gradient magnetic field pulse 604 is set so as to meet the following formula (2).

$$Ta' = Ta + Delay \qquad (2)$$

As described above, a dynamic range can be reduced by setting a time difference Delay and supplying the same waveform signal to each of the gradient magnetic field power sources 132a and 132b from the signal generation supply unit 211. In particular, by setting the time difference Delay to Tm/2, the dynamic range can be reduced the most.

Additionally, a specific reduction rate of the dynamic range depends on the imaging object and the imaging conditions, and a reduction degree of a spatial resolution in the present embodiment also depends on the imaging object and the imaging conditions. Based on the experience, appropriate Delay is about 5% of Ta.

<Embodiment>

Figure 9:
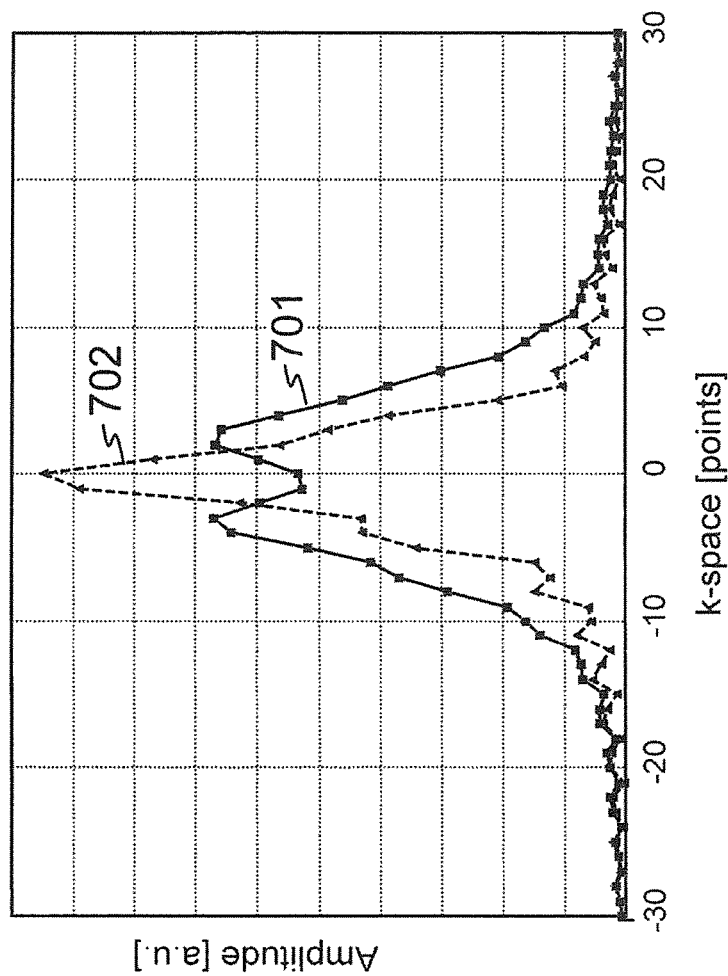
FIG. 9 is an explanatory view for explaining amplitude profiles of reception NMR signals of the first embodiment.

Here, shown are amplitude profiles of reception NMR signals to be obtained in case of actually driving the two gradient magnetic field coils 131a and 131b at different timings. FIG. 9 shows an amplitude profile 701 of reception NMR signals obtained by shifting between both the timings of supplying driving electric currents to the gradient magnetic field coils 131a and 131b, i.e. timings of applying frequency encoding gradient magnetic field pulses from the gradient magnetic field coils 131a and 131b by 30 μs as well as an amplitude profile 702 reception NMR signals obtained in case of applying the frequency encoding gradient magnetic field pulses without shifting the timings. Also, both the signals were amplified with the same reception gain.

Also, FIG. 10(a) shows an enlarged display 801 of the center of k-space to be measured in case of shifting an application timing, and FIG. 10(b) shows an enlarged display 802 of the center of k-space to be measured in case of not shifting an application timing. Also, FIGS. 10(c) and 10(d) show a phase image 803 obtained by performing the inverse Fourier transform for k-space shown in FIG. 10(a) and a phase image 804 obtained by performing the inverse Fourier transform for k-space shown in FIG. 10(b) respectively. Furthermore, FIGS. 10(e) and 10(f) show an absolute value image 805 obtained by performing the inverse Fourier transform for k-space shown in FIG. 10(a) and an absolute value image 806 obtained by performing the inverse Fourier transform for k-space shown in FIG. 10(b) respectively.

As shown in FIGS. 9, 10(a), and 10(b), when the two gradient magnetic field coils 131a and 131b are driven at different timings, peaks of reception NMR signals are reduced, which narrows a dynamic range compared to a case of driving the coils at the same timing. Also, as shown in FIGS. 10(c) and 10(d), the phase images 803 and 804 to be obtained by performing the inverse Fourier transform for k-space in which those reception NMR signals are arranged are different. That is, both of the phase distributions are different. On the other hand, as shown in FIGS. 10(e) and 10(f), the absolute value images 805 and 806 are almost the same.

Therefore, according to the method of the present embodiment, it is shown that an absolute value image is not changed while a phase image is changed even when a dynamic range of an NMR signal is changed.

As described above, the MRI apparatus 100 of the present embodiment comprises the gradient magnetic field application unit 200 that applies gradient magnetic field pulses having different waveforms according to the spatial position on the gradient magnetic field application axis in an imaging region, and the waveforms are determined by a variation amount in the time direction of magnetic field strength per unit distance.

The gradient magnetic field application unit comprises a pair of the gradient magnetic field coils 131a and 131b as well as the drive unit 210 that supplies driving electric currents having different integration values to an arbitrary time to the pair of the gradient magnetic field coils 131a and 131b respectively.

The drive unit 210 comprises the signal generation supply unit 211 and a pair of the gradient magnetic field power sources 132a and 132b, the signal generation supply unit 211 generates waveform signals instructing to apply gradient magnetic field pulses according to the predetermined pulse sequence and supplies the said waveform signals to each of the gradient magnetic field power sources 132a and 132b so that integration values to an arbitrary time are different, and the pair of the gradient magnetic field power sources 132a and 132b is connected to the pair of the gradient magnetic field coils 131a and 131b respectively to supply driving electric currents to the said gradient magnetic field coils 131a and 131b according to the waveform signals.

The signal generation supply unit 211 supplies the generated waveform signals to each of the gradient magnetic field power sources 132a and 132b at different timings.

The present embodiment comprises a gradient magnetic field application unit that applies two or more gradient magnetic field pulses composed of waveforms different from each other according to the spatial position on the gradient magnetic field application axis in an imaging region and provides an MRI apparatus in which the gradient magnetic field application unit applies gradient magnetic field pulses with two or more different waveforms and applies gradient magnetic field pulses composed of one predetermined waveform.

The present embodiment narrows a dynamic range (amplitude) of an NMR signal to be received by a reception coil (reception NMR signal) in the MRI apparatus 100. In order to narrow the amplitude of the reception NMR signal, according to the position of the imaging region, the present embodiment shifts a peak position of the NMR signal from the said position. The shift is achieved by applying frequency encoding gradient magnetic field pulses whose waveforms are different according to the position. This is achieved by supplying driving electric currents according to the same waveform signal to a pair of gradient magnetic field coils that can be driven independently at different timings.

According to the present embodiment, a dynamic range of an NMR signal to be measured is narrowed, and reception gain for the said NMR signal can be increased. Therefore, a ratio of noise superimposed in a reception system can be reduced, which additionally reduces a quantization error in AD conversion. Also, the processes of the present embodiment affects phase values only. Therefore, this does not affect absolute value images, and high quality images with a high SNR can be obtained.

As described above, the advantages of the present embodiment to the prior art are as follows.

In the prior method, reception gain is changed and an NMR signal is measured a plurality of times in order to handle an NMR signal having a wide dynamic range, which extends the measurement time. On the other hand, because a dynamic range of the NMR signal to be received is narrowed in the present embodiment, the measurement does not need to be performed a plurality of times while changing the reception gain, which does not extend the measurement time.

Also, the method of using companding according to non-patent literature 1 increases hardware costs because a non-linear amplifier needs to be inserted. On the other hand, the present embodiment does not increase the hardware costs by dividing the gradient magnetic field generating system 130 into two.

Additionally, two gradient magnetic field power sources are required to divide the gradient magnetic field generating system 130 into two.

However, the two power sources with a half output performance are provided instead of one high-output power source, which does not increase the costs. Also for software processing costs, the present embodiment does not need to add special processing at all, which does not increase the processing costs.

Therefore, the present embodiment can narrow a dynamic range of an NMR signal without extending measurement time and increasing hardware costs and software processing costs and improve an SNR and accuracy of an image.

Additionally, although the signal generation supply unit 211 controls timings for supplying signal waveforms to the gradient magnetic field power sources 132a and 132b, driving electric currents, whose time integration values to an arbitrary time are different, are supplied to the gradient magnetic field coils 131a and 131b to drive each of them in the present embodiment, and the configuration is not limited to this. For example, it may be configured so that the signal generation supply unit 211 changes shapes of generated waveform signals, generates different-shaped waveform signals, and supplies them to a pair of the gradient magnetic field power sources 132a and 132b respectively. The signal generation supply unit 211, for example, changes the shapes of waveform signals in rising and falling portions and generates the different-shaped waveform signals.

<<Second Embodiment>>

Next, a second embodiment of the present invention will be described. The first embodiment realizes the two gradient magnetic field generating systems 130 using two gradient magnetic field power sources. On the other hand, the present embodiment realizes the two gradient magnetic field generating systems 130 using a single gradient magnetic field power source and a delay circuit.

Hereinafter, the present embodiment will be described by mainly focusing on a different configuration from the first embodiment.

<Apparatus Configuration>

Figure 11:
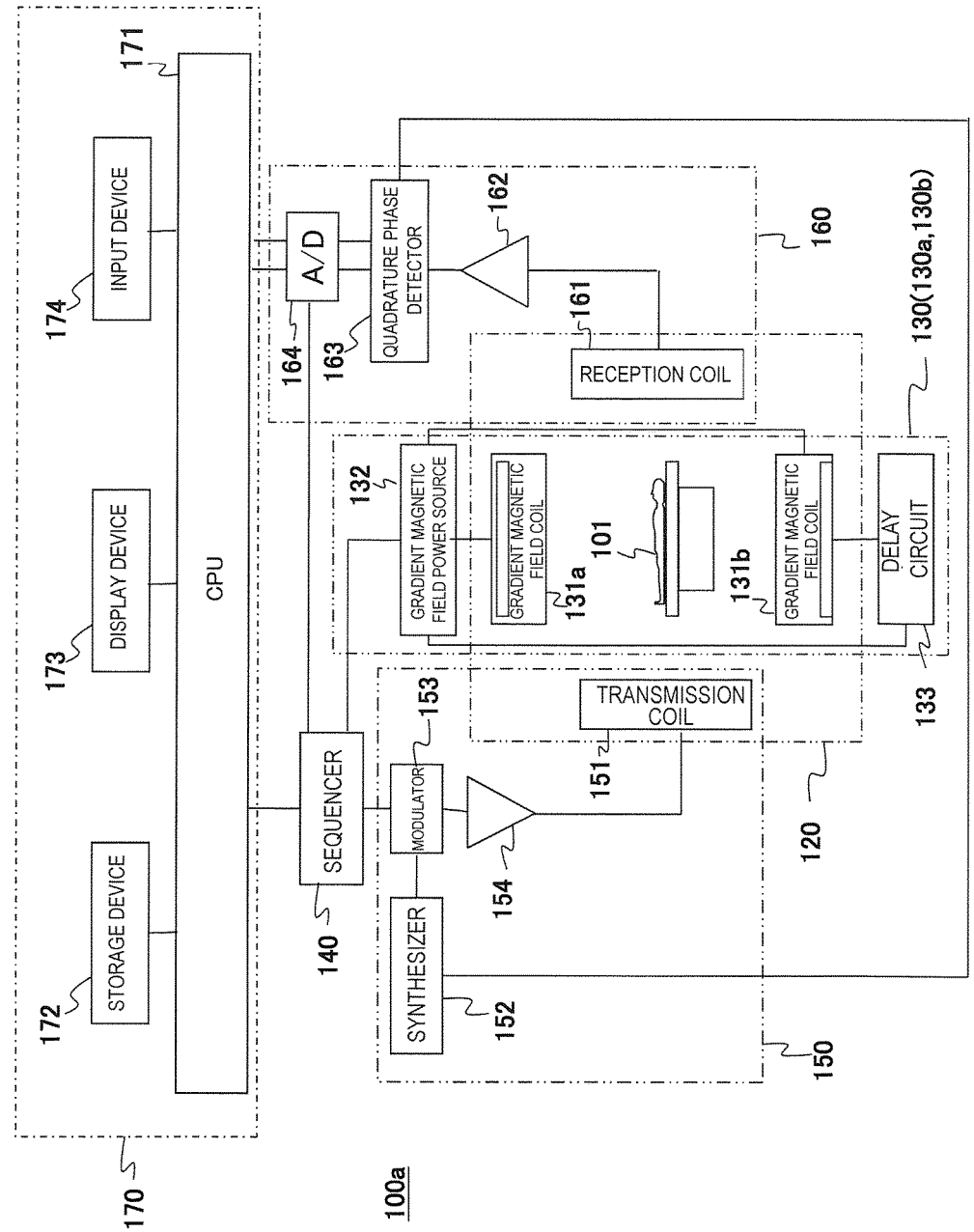
FIG. 11 is a block diagram of the MRI apparatus of a second embodiment.

FIG. 11 is a block diagram of the MRI apparatus 100a of the present embodiment. As shown in the present figure, the gradient magnetic field generating system 130 of the MRI apparatus 100a of the present embodiment comprises the one gradient magnetic field power source 132, a first gradient magnetic field coil 131a, a second gradient magnetic field coil 131b, and a delay circuit 133. The other configuration is similar to the first embodiment.

Figure 12:
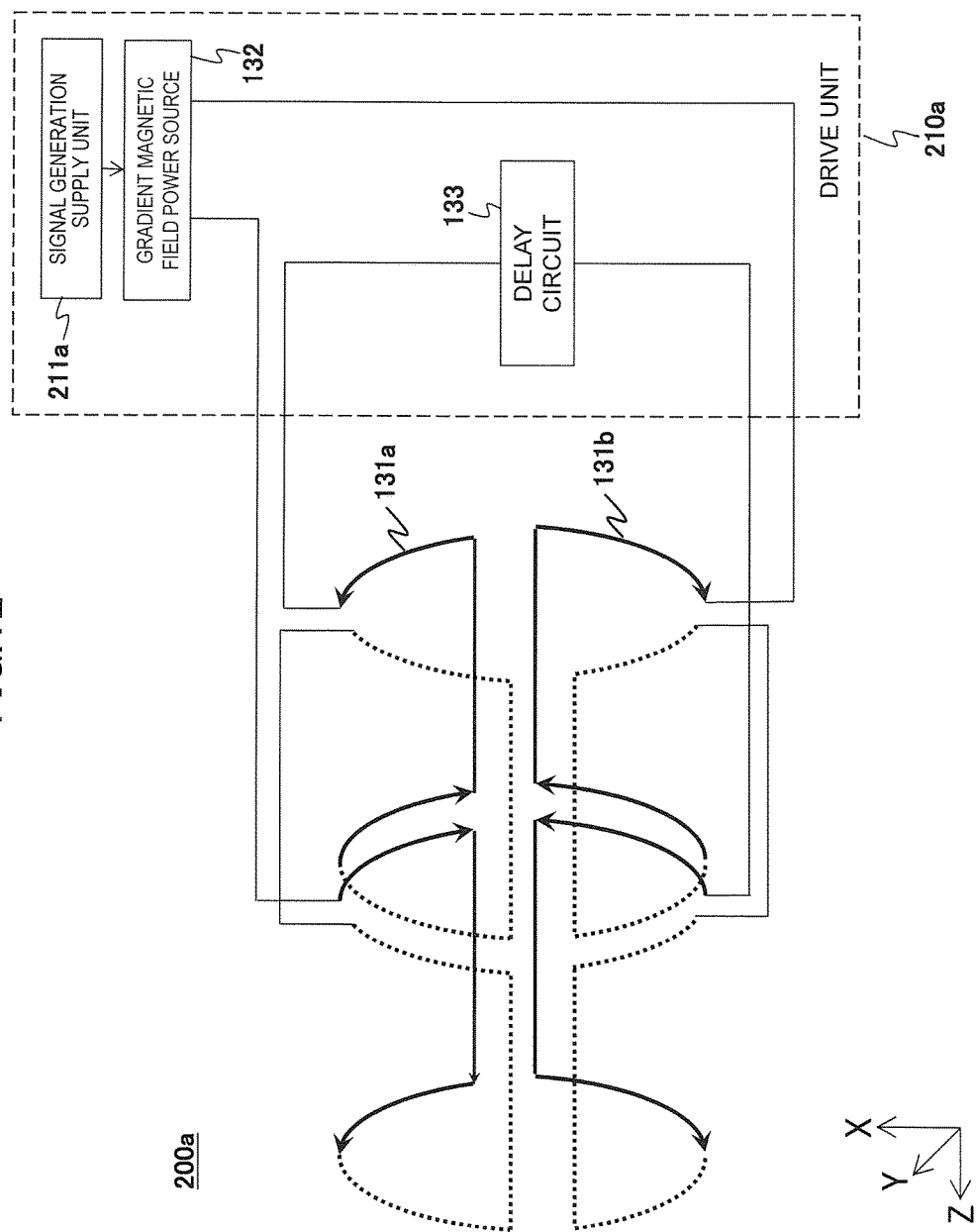
FIG. 12 is a block diagram of the gradient magnetic field application unit of the second embodiment.

<Gradient Magnetic Field Application Unit>
Similarly to the first embodiment, the present embodiment also realizes a gradient magnetic field application unit 200a that applies different-shaped gradient magnetic field pulses using the control processing system 170, the sequencer 140, and the gradient magnetic field generating system 130 according to the spatial position on the gradient magnetic field application axis in an imaging region. Then, similarly to the first embodiment, the gradient magnetic field application unit 200a of the present embodiment comprises a pair of the gradient magnetic field coils 131a and 131b and a drive unit 210a that supplies driving electric currents having different integration values to an arbitrary time to the pair of the gradient magnetic field coils 131a and 131b respectively as shown in FIG. 12. Additionally, as an example, only the X-axis direction is shown here.

As shown in the present figure, the drive unit 210a of the present embodiment comprises a signal generation supply unit 211a, a gradient magnetic field power source 132, and a delay circuit 133, and the signal generation supply unit 211a generates waveform signals instructing to apply gradient magnetic field pulses according to the predetermined pulse sequence to supply to the gradient magnetic field power source 132; the gradient magnetic field power source 132 supplies a driving electric current to one of a pair of the gradient magnetic field coils 131a and 131b according to the waveform signal; and the delay circuit 133 delays the driving electric current supplied to one gradient magnetic field coil by the gradient magnetic field power source 132 to supply a driving electric current to the other gradient magnetic field coil. As shown in the present figure, the gradient magnetic field power source 132, the gradient magnetic field coil 131a, the delay circuit 133, and the gradient magnetic field coil 131b are connected in series in this order in the present embodiment.

For example, a CR circuit, which functions as an analog low-pass filter and is composed of a resistance and a condenser, is used as the delay circuit 133.

Figure 13:
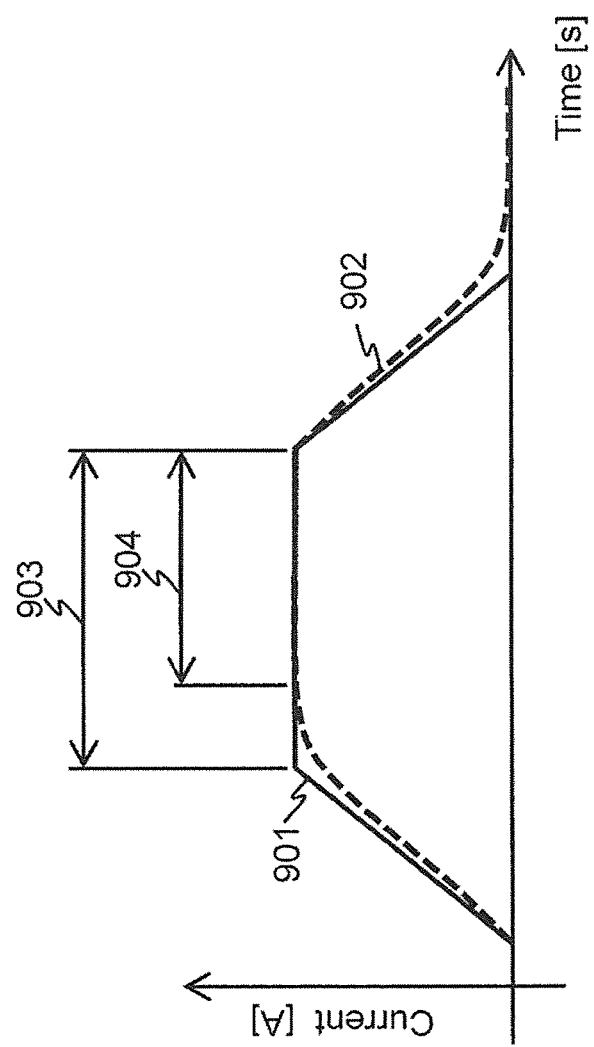
FIG. 13 is an explanatory view for explaining driving electric currents to be supplied to a pair of the respective gradient magnetic field coils of the second embodiment.

FIG. 13 shows waveforms of driving electric currents to be obtained when the low-pass filter is used as the delay circuit 133. In the present figure, a driving electric current 901 is a waveform of a driving electric current to be supplied to the gradient magnetic field coil 131a, and an electric driving current 902 is a waveform of a driving electric current to be supplied to the gradient magnetic field coil 131b via the delay circuit 133 of the low-pass filter. Also, 903 is a plateau portion of the driving electric current 901, and 904 is a plateau portion of the driving electric current 902.

As shown in the present figure, the waveforms of the driving electric currents flowing in the gradient magnetic field coils 131a and 131b are different in the present embodiment. That is, the driving electric currents having different integration values to an arbitrary time are supplied to the pair of the gradient magnetic field coils 131a and 131b.

Hence, gradient magnetic field pulse waveforms generated from the gradient magnetic field coils 131a and 131b respectively are also different. Particularly in rising and falling portions of the gradient magnetic field pulse, gradient magnetic field pulses whose strength change modes are different are applied from the gradient magnetic field coils 131a and 131b respectively. Hence, gradient magnetic field pulses whose waveforms are different are applied according to the spatial position on the gradient magnetic field application axis in an imaging region in the present embodiment.

As described above, the MRI apparatus 100a of the present embodiment comprises the drive unit 210a similarly to the first embodiment. The drive unit 210a comprises the signal generation supply unit 211a, the gradient magnetic field power source 132, and the delay circuit 133; the signal generation supply unit 211a generates waveform signals instructing to apply gradient magnetic field pulses according to the predetermined pulse sequence to supply to the gradient magnetic field power source 132; the gradient magnetic field power source 132 supplies a driving electric current to one of the pair of the gradient magnetic field coils 131a and 131b according to the waveform signal; and the delay circuit 133 delays the driving electric current supplied to the one gradient magnetic field coil by the gradient magnetic field power source 132 to supply the driving electric current to the other gradient magnetic field coil.

In the first embodiment, driving electric currents with the same waveform are supplied to the two gradient magnetic field coils 131a and 131b at different timings. However, in the present embodiment, driving electric currents with different waveforms are supplied to the two gradient magnetic field coils 131a and 131b.

Both a shift between application timings in the first embodiment and a difference between input waveforms of the present embodiment are the same for causing a phenomenon in which waveforms of gradient magnetic field pulses to be applied are different according to the position. Therefore, the method of the present embodiment can also reduce a dynamic range of a reception NMR signal similarly to the first embodiment.

Therefore, similarly to the present embodiment, reception gain to the reception NMR signal can be increased, which can obtain a high-quality image with a low SNR.

Furthermore, according to the present embodiment, the dynamic range of the reception NMR signal can be reduced using a single gradient magnetic field power source 132 by inserting the delay circuit 133 between the two gradient magnetic field coils 131a and 131b. Therefore, the above effects can be obtained by performing minor alterations for an existing MRI apparatus.

Additionally, while application timings from the two gradient magnetic field coils 131a and 131b are changed only for frequency encoding gradient magnetic field pulses in the first embodiment, driving electric currents with different waveforms are input to the two gradient magnetic field coils 131a and 131b when all the gradient magnetic field pulses are applied in the present embodiment.

Also, while time of a plateau portion of a frequency encoding gradient magnetic field pulse is shortened by shift time between the application timings in the first embodiment, the plateau portion 904 is changed (shortened) according to the response of a delay circuit as shown in FIG. 13 in the present embodiment.

Additionally, the present invention is not limited to the above-described embodiments. For example, without dividing a gradient magnetic field coil into two, the gradient magnetic field coil that can apply different gradient magnetic field pulses according to the position may be used.

Also, although a case of providing a pair of gradient magnetic field coils in each axis direction is described as an example in the above respective embodiments, the number of gradient magnetic field coils is not limited to this. Two or more gradient magnetic field coils that can be controlled independently may be used.

Also, in the above respective embodiments, frequency encoding gradient magnetic field pulses of trapezoidal waves can be applied, and using them in a certain pulse sequence is not limited.

REFERENCE SIGNS LIST

100: MRI apparatus
100a: MRI apparatus
101: object
120: static magnetic field generating system
130: gradient magnetic field generating system
130a: gradient magnetic field generating system
130b: gradient magnetic field generating system
131: gradient magnetic field coil
131a: gradient magnetic field coil
131b: gradient magnetic field coil
132: gradient magnetic field power source
132a: gradient magnetic field power source
132b: gradient magnetic field power source
133: delay circuit
140: sequencer
150: transmission system
151: transmission coil
152: high-frequency oscillator (synthesizer)
153: modulator
154: high-frequency amplifier
160: reception system
161: reception coil
162: signal amplifier
163: quadrature phase detector
164: A/D converter
170: control processing system
171: CPU
172: storage device
173: display device
174: input device
200: gradient magnetic field application unit
200a: gradient magnetic field application unit
210: drive unit
210a: drive unit
211: signal generation supply unit
211a: signal generation supply unit
301a: magnetic field distribution by the gradient magnetic field coil 131a
301b: magnetic field distribution by the gradient magnetic field coil 131b
302: synthesized magnetic field distribution
400: driving electric current
401: driving electric current
402: driving electric current
410: gradient magnetic field pulse
411: gradient magnetic field pulse
412: gradient magnetic field pulse
420: gradient magnetic field pulse
421: gradient magnetic field pulse
422: gradient magnetic field pulse
501: gradient magnetic field pulse
502: gradient magnetic field pulse
503: gradient magnetic field pulse
504: gradient magnetic field pulse
505: gradient magnetic field pulse
511: plateau portion
512: plateau portion
600: pulse sequence
601: RF pulse
602: slice selection gradient magnetic field pulse
603: phase encoding gradient magnetic field pulse
604: frequency encoding gradient magnetic field pulse
605: spare time between repetition times
606: time of a plateau portion
701: amplitude profile
702: amplitude profile
801: enlarged display of the k-space center
802: enlarged display of the k-space center
803: phase image
804: phase image
805: absolute value image
806: absolute value image
901: driving electric current
902: electric driving current
903: plateau portion
904: plateau portion

The invention claimed is:

1. A magnetic resonance imaging apparatus, comprising:
a gradient magnetic field application unit that applies two or more gradient magnetic field pulses composed of respective waveforms different from each other, according to respective spatial positions on a single gradient magnetic field application axis in an imaging region,
wherein the gradient magnetic field pulses with two or more different waveforms applied by the gradient magnetic field application unit on the single gradient magnetic field application axis are generated based on one predetermined waveform.

2. The magnetic resonance imaging apparatus according to claim 1,
wherein the gradient magnetic field application unit applies gradient magnetic field pulses so as to have different waveforms according to the respective spatial positions on the single gradient magnetic field application axis in the imaging region, and
wherein the different waveforms are determined by a variation amount in the time direction of magnetic field strength per unit distance.

3. The magnetic resonance imaging apparatus according to claim 2,
wherein the gradient magnetic field pulses are trapezoidal waves, and
wherein the gradient magnetic field application unit applies gradient magnetic field pulses having different shapes, in the rising and falling portions according to the spatial position on the single gradient magnetic field application axis.

4. The magnetic resonance imaging apparatus according to claim 2, wherein the gradient magnetic field application unit comprises:
a pair of gradient magnetic field coils configured for the single gradient magnetic field application axis; and
a drive unit that supplies driving electric currents, whose integration values to an arbitrary time are different, to the pair of gradient magnetic field coils respectively.

5. The magnetic resonance imaging apparatus according to claim 4,
wherein the drive unit supplies the driving electric currents so as to have a period when only one of the pair of gradient magnetic field coils is driven.

6. The magnetic resonance imaging apparatus according to claim 4,
wherein the drive unit comprises:
a signal generation supply unit; and
a pair of gradient magnetic field power sources,
wherein the signal generation supply unit generates waveform signals instructing to apply gradient magnetic field pulses according to a predetermined pulse sequence and supplies the generated waveform signals to each of the gradient magnetic field power sources so that integration values to an arbitrary time are different, and wherein the pair of gradient magnetic field power sources is connected to the pair of the gradient magnetic field coils respectively to supply driving electric currents to the said gradient magnetic field coils according to the waveform signals.

7. The magnetic resonance imaging apparatus according to claim 6, wherein the signal generation supply unit supplies the generated waveform signals to each of the gradient magnetic field power sources at different timings.

8. The magnetic resonance imaging apparatus according to claim 6, wherein the signal generation supply unit changes shapes of the generated waveform signals and supplies them to each of the gradient magnetic field power sources.

9. The magnetic resonance imaging apparatus according to claim 4, wherein the drive unit comprises:

a signal generation supply unit;

gradient magnetic field power sources; and a delay circuit, wherein the signal generation supply unit generates waveform signals instructing to apply gradient magnetic field pulses according to a predetermined pulse sequence and supplies the generated waveform signals to the gradient magnetic field power sources, wherein the gradient magnetic field power sources supply driving electric currents to one of the pair of gradient magnetic field coils according to the waveform signal, and wherein the delay circuit delays the driving electric current supplied to the one gradient magnetic field coil by the gradient magnetic field power sources to supply the driving electric current to the other gradient magnetic field coil.

10. The magnetic resonance imaging apparatus according to claim 4, wherein the gradient magnetic field coils are respectively provided in each axis direction in pairs, and wherein, when frequency encoding gradient magnetic field pulses are applied, the drive unit supplies the driving electric currents to the pair of gradient magnetic field coils in the axis direction to apply the said frequency encoding gradient magnetic field pulses.

11. The magnetic resonance imaging apparatus according to claim 9, wherein a CR circuit, which functions as a low-pass filter and is composed of a resistance and a condenser, is used as the delay circuit.

* * * * *